United States Patent
Naggi et al.

(10) Patent No.: US 6,329,351 B1
(45) Date of Patent: Dec. 11, 2001

(54) SEMI-SYNTHETIC SULPHAMINOHEPAROSANSULPHATES HAVING HIGH ANTI-METASTATIC ACTIVITY AND REDUCED HAEMORRHAGIC RISK

(75) Inventors: Annamaria Naggi, Legnano; Giangiacomo Torri, Milan, both of (IT)

(73) Assignee: Istituto Scientifico Di Chimica E Biochimica "G. Ronzoni", Milan (IT)

( * ) Notice: Subject to any disclaimer, the term of this patent is extended or adjusted under 35 U.S.C. 154(b) by 0 days.

(21) Appl. No.: 09/254,128
(22) PCT Filed: Aug. 28, 1997
(86) PCT No.: PCT/EP97/04682
  § 371 Date: Dec. 20, 1999
  § 102(e) Date: Dec. 20, 1999
(87) PCT Pub. No.: WO98/09636
  PCT Pub. Date: Mar. 12, 1998
(51) Int. Cl.[7] .......... A61K 31/715; C08B 37/10
(52) U.S. Cl. .......... 514/56; 536/21
(58) Field of Search .......... 536/21; 514/56

(56) References Cited

U.S. PATENT DOCUMENTS 5,550,116 * 8/1996 Lormeau et al. .......... 514/56

FOREIGN PATENT DOCUMENTS 9429352  12/1994  (WO) .

OTHER PUBLICATIONS

TIPS, Jun. 1995 (vol. 16) 199–203.
Heparin and Related Polysaccharides, Lane et al. (1992) 317–327.
Carbohydrate Research 263 (1994) 271–284.

* cited by examiner

Primary Examiner—Kathleen Kebler Fonda
(74) Attorney, Agent, or Firm—Hedman & Costigan, P.C.

(57) ABSTRACT

Sulphaminoheparosansulphates obtainable from the *Escherichia coli* K5 polysaccharide by deacetilation and the subsequent sulfation with the sulphuric anhydride/trimethylamine adduct carried out at 0° C., for times ranging from 0.25 to 2 hours and using a reactant/polysaccharide ratio ($SO_3$ equivalents/available OH groups equivalents) equal to 5 have been found having high anti-metastatic activity and low anticoagulant activity.

4 Claims, No Drawings

SEMI-SYNTHETIC SULPHAMINOHEPAROSANSULPHATES HAVING HIGH ANTI-METASTATIC ACTIVITY AND REDUCED HAEMORRHAGIC RISK

This application is a U.S. National Stage entry under 35 U.S.C. §371 of PCT/EP97/04682, filed Aug. 28, 1997.

The object of the present invention is the use of the sulphaminoheparosansulphates as anti-metastatic agents.

The metastasis is a process consisting of the detachment of cancer cells from the site of the primary cancer, the dissemination in the blood flow, the adhesion to the vascular walls, and the migration and growth in extra-vascular spaces. Said phenomena, and in particular the adhesion to the vascular walls, seem to be regulated by the endogenous heparan sulfate (HS) polysaccharide. Some anticoagulant drugs, among which the heparin (HEP), which shows structural analogies with the heparan sulfate, have been tested as potential anti-metastatic agents. (I. Vlodavsky et al.: "Modulation of neovascularization and metastasis by species of heparin", in: "Heparin and Related Polysaccharides" (D. A. Lane et al., Eds.), Plenum Press, New York 1992, 317–327). The heparin among said drugs is particularly active as anti-metastatic, but its high anticoagulant activity implies haemorrhagic risks, whereby the search for heparin-like substances having reduced anticoagulant activity is particularly interesting. (D. J. Tyrrell et al.: "Therapeutic uses of heparin beyond its traditional role as an anticoagulant", TIPS 16, 198–204, 1995).

With the present invention we have found that some semi-synthetic heparan sulfates belonging to the sulphaminoheparosansulphates (SAHS) class (B. Casu et al.,: "Heparin-like compounds prepared by chemical modification of capsular polysaccharide from *E. coli* K5", Carbohydr. Res. 263, 271–284 (1994)), surprisingly carry on an "in vivo" anti-metastatic activity comparable to the heparin one, even if having an "in vivo" anticoagulant activity an order of magnitude lower than the heparin one.

More particularly, we have found that only the SAHS obtainable from the *Escherichia coli* K5 polysaccharide by deacetilation and subsequent sulfation with the sulphuric anhydride/trimethylamine adduct carried out at 0° C., for times ranging from 0.25 to 2 hours and using a reactant/polysaccharide ratio ($SO_3$ equivalents/available OH groups equivalents) equal to 5 (named SAHS-B), having molecular weight ranging from 5,000 to 40,000, show anti-metastatic activity comparable to a typical heparin one, while SAHS prepared according to other experimental conditions have anti-metastatic activity notably lower either than the heparin one or than the SAHS-B one.

Moreover we have also found that fractions of SAHS-B having a molecular weight lower than 5,000 keep a significant anti-metastatic activity (also greater than the one of the corresponding heparins having low molecular weight).

Therefore the semi-synthetic SAHS-B heparosansulfates look as anti-metastatic drugs having a reduced haemorrhagic risk.

For the purpose, the SAHS-B will be formulated in suitable pharmaceutical compositions, using conventional techniques and excipients. Such compositions may be administered for the prevention or the therapy of metastases in doses which will obviously depend from several factors but which will be generally ranging from 1 to 1,000 mg of SAHS-B one or more times a day.

The SAHS have been obtained as previously described (B. Casu et al., 1994, loc. cit.; PCT/EP94/01660) from the K5 polysaccharide, which is a constituent of the cell membrane of the Escherichia coli K5 strain. In particular, the K5 polysaccharide has been selectively N-deacetilated and N-sulfated, and then O-sulfated as summarily described in the following scheme, obtaining the SAHS of different kind SAHS-B, SAHS-C, SAHS-A.

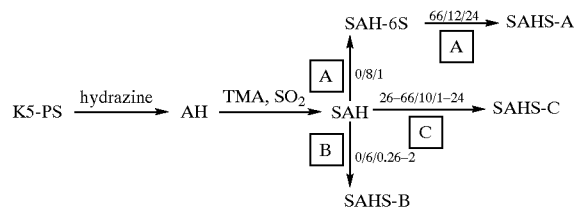

Scheme

The first step consists of the N-deacetilation by hydrazinelysis of the K5 polysaccharide (K5-PS). The obtained product (heparosan, AH) is N-sulfated with the sulphuric anhydride/trimethylamine adduct (TMA/$SO_3$), with the achievement of the sulphaminoheparosan (SAH). The numbers near the arrows show in order the reaction temperatures (° C.), the reactant/polysaccharide ratios ($SO_3$ equivalents/equivalents of available hydroxyl groups), and the reaction times (hours).

The anti-metastatic activity of the SAHS, heparin and other reference sulfated polysaccharides has been tested using the method of the colonization to the lung of B16B16 melanoma cells. (N. Caselia et al., Thromb. Haem. 73,964 (1995)). Such a method, lending itself particularly to test the effect of the drugs with inhibitory activity on the cancer haematic dissemination, consists of the evaluation of the number of the cancer colonies which form in the lung after the injection of murine melanoma cells by intravenous way in the mouse. B16B16 melanoma cells have been used. The cells have been cultured in DME with 10% of fetal bovine serum in a $CO_2$ (5%) incubator in humidity conditions and at 37° C. The cells have been divided two times a week, treating them with 0.25% trypsin/0.05% EDTA. The polysaccharides to test have been dissolved in physiological solution or in phosphate (PBS) buffer, at the proper dilution, and used on the spot. B16B16 melanoma cells, diluted in PBS ($10^5$ cells/0.1 ml/mouse) have been injected into a side vein of the tail of C57B16 mice having an average weight equal to 20 g, in a final volume equal to 0.2 ml/mouse. The mice have been sacrificed 12–16 days after the injection of the cancer cells; the lungs have been taken and fixed in a Buoin solution for the count of the superficial metastatic nodules, which are pointed out as black masses on a yellow ground. Then the ratio between the number of lung nodules in the treated mice and in the control ones has been estimated. Each experiment has been carried out on a minimum number of five mice, more frequently on 8–10 mice. The inhibition percentages of the metastases discovered in several experiments have been reported in the individual Examples and in Table 1.

EXAMPLE 1

Preparation and anti-metastatic activity of type A, B and C SAHS

Standard procedures for the preparation of some sulphaminoheparosansulphates having different anti-metastatic activity are hereinafter described. The products have been characterized with respect to the average molecular weight (by gel filtration), sulfation degree (expressed as sulfates/ carboxyles molar ratio, determined by conductimetry), and distribution of the sulfate groups (determined by $^1$H and $^{13}$C NMR spectrometry), as described in Casu et al., 1994 (loc. cit.). The procedures described hereinbelow take to SAHS having a N-sulfation degree about equal to 100%, and a 6-O-sulfation degree at least equal to 25%.

The starting K5 polysaccharide may be suitably prepared as described in the Italian Patent Application M191A000659.

The quantities in brackets are indicative.

1a) N-deacetilation

The K5 polysaccharide (100 mg) and hydrazine sulfate (138 mg) are dissolved in anhydrous hydrazine (1.38 mg) and maintained in a closed pipe, under nitrogen atmosphere, for 5 hours at 96° C. The solution is dried in a rotating evaporator, the reaction product is dissolved in distilled water and the pH is taken to 4 with 37% HCl. The pH is taken to 9 with NaOH 2N and 4 volumes of ethanol saturated with sodium acetate are added. The obtained precipitate is filtered, dissolved in distilled water, and the solution is dialyzed against distilled water for 3 days (3×2l each day; cut-off 14,000 D) and finally freeze-dried.

1b) N-sulfation

The polysaccharide obtained as in 1a) (100 mg) is dissolved in distilled water, the solution pH is taken to 9 by the addition of solid sodium bicarbonate, and the temperature increased to 55° C. At this temperature, maintaining the mixture under stirring, 100 mg of trimethylamine/sulfur trioxide adduct (TMA/SO$_3$) are added. Equal amounts of the adduct are added after 4 hours, and it is left to react for a total time equal to 24 hours. The recovery of the N-sulfated polysaccharide is carried out as described above.

1c) N-sulfation

The polysaccharide obtained as in 1b) (100 mg) is dissolved in distilled water (20 ml), and the solution is passed through an Amberlite IR-120 H$^+$column at room temperature. The column is washed with other 20 ml of distilled water and the eluates are collected, which are taken to pH 5.5 with 10% tributylamine in ethanol (w/v) (3 ml). The tributylamine excess is removed with diethyl ether (40 ml) and it is freeze-dried.

The so obtained product (188.2 mg) is dissolved in anhydrous dimethylformamide (33 ml), the pyridine/sulfur trioxide adduct (Py/SO$_3$, amounts indicated below) dissolved in 15 ml of anhydrous dimethylformamide is added, and the reaction mixture is maintained at the temperatures and for the times indicated below. In order to obtain different types of SAHS, different reaction temperatures, amounts of sulfur adduct and reaction times have been adopted. In particular, the type A SAHS has been obtained working at 0° C., and using 460 mg of pyridine/SO$_3$, for 1 hour. The product (G1524-3; average molecular weight 11,700; sulfates/carboxyles molar ratio 1.8) has shown an anti-metastatic activity corresponding to 17.5% of metastasis inhibition for a dose equal to 0.5 mg/mouse; in the same test, the reference heparin has shown the 97.5% of inhibition, and 54.8% for the heparan sulfate from pig-pancreas.

The type B SAHS has been obtained working at 0° C., using 765 mg of sulfur adduct, for 0.25–2 hours (preferably 1 hour) and submitting again the product to N-resulfation as described in 1b). A typical final product (G1669; average molecular weight 25,700; sulfates/carboxyles molar ratio 2.2) has shown an anti-metastatic activity (0.5 mg/mouse dose) corresponding to 92.7% of metastasis inhibition.

The type C SAHS has been obtained working at 25° C. for 1 hour, with 7.650 mg of sulfur adduct. The product (G1524/3; average molecular weight 10,800; sulfates/carboxyles molar ratio 2.8) has shown an anti-metastatic activity (0.5 mg/mouse dose) corresponding to 8.8% of metastasis inhibition.

EXAMPLE 2

Type B SAHS anti-metastatic activity

The anti-metastatic activity tests have been repeated for the SAHS-B prepared as described in the Example 1 (product G1669), for three doses (0.5; 0.2 and 0.1 mg/mouse). The corresponding inhibitions of the metastases have been respectively 78.5%, 62.5% and 20.5%; for the same doses, the reference heparin has shown inhibitions respectively equal to 95.5%, 91.3% and 80.3%.

EXAMPLE 3

Type B SAHS anti-metastatic activity

The anti-metastatic activity test has been repeated for the type B SAHS prepared as described in the Example 1 (product G1669), for the dose 0.5 mg/mouse, showing an inhibition equal to 98.5% of the metastases. (At the same dose, the reference heparin has shown an inhibition equal to 98.5%, and for a "super-sulfated" heparin having a low molecular weight an inhibition equal to 91.0%.

EXAMPLE 4

Preparation and anti-metastatic activity of type B SAHS fractions having different molecular weight A sample of type B SAHS (preparation G1668, obtained essentially as described in the Example 1) has been fractionated by Sephadex gel chromatography, and the three fractions characterized by analogous sulfates/carboxyles (2.2–2.3) ratios and different molecular weights have been isolated: G1668a (average molecular weight 38,200), G1668c1 (22,700) and G1668b1 (3,200). The corresponding anti-metastatic activities (0.5 mg/mouse dose) turned out to be analogous for the three fractions (inhibition equal to 97–98%) and analogous to another non fractionated SAHS-B preparation (G1783) one prepared as described in the Example 1. In the same set of experiments, the reference heparin has shown an inhibition equal to 95–97%.

EXAMPLE 5

Anti-metastatic activity of low molecular weight SAHS-B

Comparison with other natural and super-sulfated glycosaminoglycans. The anti-metastatic activity of the G1668b1 fraction having low molecular weight (obtained as described in the Example 4) turned out to correspond to 83.6% of metastasis inhibition. In the same test, the reference heparin has shown an inhibition equal to 92.8%, a "super-sulfated" heparan sulfate having low molecular weight (ssLMWHS) an inhibition equal to 46.4%, and a dermatan sulfate 4.6-disulfated (DS4, 6S) an inhibition equal to 65.32%.

EXAMPLE 6

SAHS-B anti-metastatic activity

A preparation of SAHS-B (product G1668, obtained acting essentially as described in the Example 1) has shown an anti-metastatic activity (0.5 mg/mouse dose) corresponding to the 98.5% of metastasis inhibition. (In the same test, the reference heparin has given 98.5% of inhibition).

EXAMPLE 7

Anti-metastatic activity of a low dose of a low molecular weight SAHS-B fraction The low molecular weight G1668c1 fraction described in the Example 4 has shown, at the dose equal to 0.1 mg/mouse, an anti-metastatic activity corresponding to the inhibition of the 41.0% of the metastases. (At the same dose, the non fractionated reference heparin provided an inhibition equal to 91.1%).

EXAMPLE 8

Anti-metastatic activity of a very low dose of a low molecular weight SAHS-B fraction The low molecular weight G1668c1 fraction described in the Example 4 has shown, at the dose equal to 0.02 mg/mouse, an anti-metastatic activity corresponding to the inhibition of the 24% of the metastases. (At the same dose, the reference heparin inhibited 30% of the metastases).

EXAMPLE 9

Anticoagulant activity of SAHS-B

The G1668 product anticoagulant activity, determined as the prolongation of the APTT value in the mouse (intravenous injection of 0.5 mg/mouse; experiments on a group of 4 mice), turned out to be respectively >300; 44.4, and 39.9 respectively after 1, 2, and 4 hours from the injection. The corresponding values for the reference heparin have been: >300; >300, and 37.6. (Common value for the controls: 28.5).

TABLE 1

ANTI-METASTATIC ACTIVITY OF THE SULFAMINO-HEPAROSANSULFATES (SAHS)

|  | dose (mg/mouse) | inhibition % |
|---|---|---|
| N.1 | | |
| SAHS-A (G1524-3) | 0.5 | 17.5 (HEP 97.5; HS 54.8) |
| SAHS-B (G1669) | 0.5 | 92.7 |
| SAHS-C (G1655NS) | 0.5 | 8.8 |
| N.2 | | |
| SAHS-B (G1669) | 0.5 | 75.8 (HEP 95.5) |
|  | 0.2 | 62.5 (91.3) |
|  | 0.1 | 20.5 (80.3) |
| N.3 | | |
| SAHS-B (G1669) | 0.5 | 84.7 (HEP 98.5; ssLMW-LMW 91.0) |
| N.4 | | |
| LMW-SAHS-B (G1668c1) | 0.5 | 97–98 (HEP 95–97; LMW-HEP~50) |
| SAHS-B (G1668b1) | 0.5 | 97–98 |
| SAHS-B (G1668a) | 0.5 | 97–98 |

TABLE 1-continued

ANTI-METASTATIC ACTIVITY OF THE SULFAMINO-HEPAROSANSULFATES (SAHS)

|  | dose (mg/mouse) | inhibition % |
|---|---|---|
| N.5 | | |
| SAHS-B (G1783) | 0.5 | 97–98 |
| N.6 | | |
| SAHS-B (G1668b1) | 0.5 | 86.3 (HEP 92.8; ssLMW-HS 46.4; DS4, 6S 65.3) |
| N.7 | | |
| SAHS-B (G1668) | 0.5 | 97.4 (HEP 98.5) |
| N.8 | | |
| LMW-SAHS-B (G1668c1) | 0.1 | 41.0 (HEP 91.1) |
| LMW-SAHS-B (G1668c1) | 0.02 | 24 (HEP 30.0). |

What is claimed is:

1. A process for the preparation of pharmaceutical compositions having antimetastatic activity and a reduced hemorrhagic risk, containing a sulfaminoheparosan sulfate, comprising:

a) deacetylation of K5 polysaccharide from *Escherichia coli* to obtain deacetylated K5 polysaccharide;

b) sulfation of deacetylated K5 polysaccharide obtained in step a) with sulfuric anhydride/trimethylamine adduct to obtain sulfaminoheparosan sulfate, and c) formulating said sulfaminoheparosan sulfate with conventional excipients, wherein said sulfation is carried out at 0° C. for times ranging from 0.25 to 2 hours and using an adduct/polysaccharide ratio, defined as $SO_3$ equivalents/available OH groups equivalents, equal to 5.

2. A process according to claim 1, wherein said sulfaminoheparosan sulfate has an average molecular weight ranging from 3,200 to 38,200 D.

3. A process according to claim 1, wherein said sulfaminoheparosan sulfate has a sulfates/carboxyls ratio of 2.2–2.3.

4. A therapeutic method for therapy of metastases consisting in the administration to patients in need of therapy for metastases of a composition comprising a sulfaminoheparosan sulfate prepared according to claim 1, in an amount corresponding to from 1 to 1,000 mg of said sulfaminoheparosan sulfate one or more times a day.

* * * * *